(12) United States Patent
Chiba

(10) Patent No.: US 9,260,769 B2
(45) Date of Patent: Feb. 16, 2016

(54) CO-BASED ALLOYS FOR BIOMEDICAL APPLICATIONS AND STENT

(71) Applicants:Seiko Instruments Inc., Chiba-shi, Chiba (JP); Kyocera Medical Corporation, Yodogawa-ku, Osaka (JP); Tohoku University, Sendai-shi, Miyagi (JP)

(72) Inventor: Akihiko Chiba, Chiba (JP)

(73) Assignee: SEIKO INSTRUMENTS INC., Chiba (JP)

(*) Notice: Subject to any disclaimer, the term of this patent is extended or adjusted under 35 U.S.C. 154(b) by 525 days.

(21) Appl. No.: 13/622,898

(22) Filed: Sep. 19, 2012

(65) Prior Publication Data
US 2013/0073028 A1  Mar. 21, 2013

Related U.S. Application Data

(63) Continuation of application No. PCT/JP2011/056939, filed on Mar. 23, 2011.

(30) Foreign Application Priority Data

Mar. 24, 2010 (JP) .................... 2010-067973

(51) Int. Cl.
*C22C 19/07* (2006.01)
*A61F 2/82* (2013.01)
(Continued)

(52) U.S. Cl.
CPC . *C22C 19/07* (2013.01); *A61F 2/82* (2013.01); *A61L 27/045* (2013.01); *A61L 31/022* (2013.01); *C22C 1/02* (2013.01); *C22F 1/10* (2013.01)

(58) Field of Classification Search
CPC .............. C22C 19/07; C22C 1/10; A61F 2/82
USPC ............................ 148/425; 420/436
See application file for complete search history.

(56) References Cited

U.S. PATENT DOCUMENTS 3,223,522 A * 12/1965 Rausch et al. ............... 420/439
3,837,838 A *  9/1974 Mohammed ................. 420/585
(Continued)

FOREIGN PATENT DOCUMENTS

JP    56-087644 A    7/1981
JP    59-232248 A   12/1984
(Continued)

OTHER PUBLICATIONS

Sketch, Michael H., et al. "Evaluation of the Medtronic (Driver) cobalt-chromium alloy coronary stent system." The American journal of cardiology 95.1 (2005): 8-12.*
(Continued)

*Primary Examiner* — Jessee Roe
(74) *Attorney, Agent, or Firm* — Brinks Gilson & Lione; G. Peter Nichols

(57) ABSTRACT

A first object of the present invention is to provide Co-based alloys for biomedical applications which are Ni-free, high intensity and high elastic modulus and are suitable for plastic workability. Moreover, a second object of the present invention is to provide Co-based alloys for biomedical applications having X-ray visibility. Furthermore, a third object of the present invention is to provide a stent using the alloys. The Co-based alloys for biomedical applications according to the present invention is configured by adding alloy elements having biocompatibility and an effect of increasing stacking fault energy of the alloys.

1 Claim, 18 Drawing Sheets

(51) Int. Cl.
 *A61L 27/04* (2006.01)
 *A61L 31/02* (2006.01)
 *C22C 1/02* (2006.01)
 *C22F 1/10* (2006.01)

(56) References Cited

U.S. PATENT DOCUMENTS

| | | | |
|---|---|---|---|
| 4,255,190 A * | 3/1981 | Prosen | 420/436 |
| 4,606,887 A * | 8/1986 | Hausselt et al. | 420/437 |
| 2002/0041820 A1* | 4/2002 | Prasad | 420/437 |
| 2005/0232806 A1* | 10/2005 | Lindigkeit | 420/436 |
| 2008/0185075 A1* | 8/2008 | Ishida et al. | 148/538 |
| 2008/0251163 A1 | 10/2008 | Chiba et al. | |
| 2008/0281396 A1 | 11/2008 | Ishida et al. | |

FOREIGN PATENT DOCUMENTS

| | | |
|---|---|---|
| JP | 62-146233 A | 6/1987 |
| JP | 2007-162121 A | 6/2007 |
| WO | WO 2006/054368 A1 | 5/2006 |
| WO | WO 2007/043687 A1 | 4/2007 |
| WO | WO 2008/139829 A1 | 11/2008 |

OTHER PUBLICATIONS

Office Action from Japanese Application No. 2010-067973, dated Jan. 14, 2014, 8 pages.
International Search Report for International Application No. PCT/JP2011/056939, dated May 31, 2011, 2 pages.

* cited by examiner

YOUNG'S MODULUS, E/GPa

CO-BASED ALLOYS FOR BIOMEDICAL APPLICATIONS AND STENT

RELATED APPLICATIONS

This application is a continuation of PCT/JP2011/056939 filed on Mar. 23, 2011, which claims priority to Japanese Application No. 2010-067973 filed on Mar. 24, 2010. The entire contents of these applications are incorporated herein by reference.

BACKGROUND OF THE INVENTION

1. Field of the Invention

The present invention relates to Co-based alloys for biomedical applications and in particular, to Co-based alloys for biomedical applications which are suitably provided for use of medical equipment such as equipment embedded-in a living body and equipment which has contact with the living body. In addition, the present invention relates to a stent.

2. Description of the Related Art

For alloys which are used for medical equipment embedded-in a living body or for medical equipment used while being in direct contact with the surface of the living body, high corrosion resistance and biocompatibility are required. Furthermore, with respect to alloys for a stent for securing blood flow by expanding coarctation site of a blood vessel within a living body, high intensity and high elastic modulus are required.

As Co-based alloys for biomedical applications which satisfy such requirements described above, alloys which consist primarily of Co-20 Cr-15W-10Ni (ASTM standard F90), alloys which contain the following, Co: 30% to 60%, Ni: 4% to 20%, Cr: 13% to 25%, C: equal to or less than 0.3%, Si: equal to or less than 2.0% and Mn: equal to or less than 2.0% or the like are well known (refer to PTL 1).
Patent Literature: [PTL 1] JP-A-2007-162121

SUMMARY OF THE INVENTION

In the ASTM standard F90 alloys or the alloys disclosed in PTL 1, Ni is included and when considering allergies to a living body caused by Ni, there is demand for development of Ni-free alloys.

However, Ni is added to improve plastic workability and is an additive element which is necessary to give high plastic workability such as a tube process which is necessary to perform a process to the stent, for example. Therefore, in composition of the alloys described above, when Ni-free alloys are made, there is a problem in that performance of the plastic workability or the like is noticeably lowered.

In addition, in order to verify the location of the stent through fluoroscopy when the stent is introduced in the living body, as alloys for a stent, a material having high X-ray visibility is demanded. However, since the stent is introduced inside a thin blood vessel, the thickness of a tube-shaped stent is processed to be extremely thin, therefore, in alloy compositions in the related art, the X-ray visibility is not sufficient and further improvement of the X-ray visibility is demanded.

The present invention is made to consider such circumstances in the related art, and a first object is to provide Co-based alloys for biomedical applications which have a high intensity (high tensile strength), high elastic modulus and are suitable for plastic workability. Moreover, a second object of the present invention is to provide Co-based alloys for biomedical applications having X-ray visibility. In addition, a third object of the present invention is to provide a stent using the corresponding alloys.

In order to solve the problems described above, Co-based alloys for biomedical applications according to the present invention includes biocompatibility in Co—Cr—W system alloys and are formed to add alloy elements which have an effect of causing stacking fault energy of the alloys to increase.

It is preferable that the alloy element be one type or two types selected from a group consisting of Nb, Ta and Fe.

It is more preferable that the alloy element be Nb and/or Ta.

Furthermore, it is preferable that the Co-based alloys for biomedical applications contain the following, Cr: 5% by mass to 30% by mass and W: 5% by mass to 20% by mass.

In addition, it is preferable that the addition amount of the alloy element be equal to or less than 3% by mass. The Co-based alloys for biomedical applications of the present invention can be used for the stent. Furthermore, according to the present invention, the stent which is formed by using the Co-based alloys for biomedical applications is provided.

In the Co-based alloys for biomedical applications according to the present invention, by adding, to the Co—Cr—W system alloys, alloy elements which have biocompatibility and have an effect of increasing stacking fault energy of the alloys, it is possible to stabilize a $\gamma$ phase of the alloys, to prevent the occurrence of an $\epsilon$ phase of a strain induction martensite at a process stage and to improve plastic workability. In addition, since Ni is not contained in the Co-based alloys for biomedical applications of the present invention, there is no possibility that allergies of Ni may be incurred to the living body.

Furthermore, since the Co-based alloys for biomedical applications of the present invention is a composition configured by adding one type or two types or more elements selected from a group consisting of Nb, Ta and Fe to Co—Cr—W system alloys, it is possible not only to improve plastic workability of Co-based alloys but also improve elastic modulus and tensile strength. Moreover, since the Co-based alloys for biomedical applications of the present invention is configured by adding high density elements such as Nb and/or Ta, X-ray visibility of the alloys can be increased and the Co-based alloys for biomedical applications can be suitably used as alloys for a stent.

Since the stent according to the present invention is configured by using the Co-based alloys for biomedical applications of the present invention, allergies caused by Ni are not incurred and the stent has favorable elastic modulus and tensile strength. In addition, since the stent is formed by the Co-based alloys for biomedical applications of the present invention to which Nb and/or Ta is added, the stent which has more favorable X-ray visibility can be obtained.

BRIEF DESCRIPTION OF THE DRAWINGS

FIG. 7(a) shows a structure through an optical microscope of Co-20Cr10W, FIG. 7(b) shows a structure through an optical microscope of Co-20Cr-10W-1Nb and FIG. 7(c) shows a structure through an optical microscope of Co-20Cr-10W-2Nb.

FIG. 9(a) shows a structure through an optical microscope of Co-20Cr-10W, FIG. 9(b) shows a structure through an optical microscope of Co-20Cr-10W-1Nb and FIG. 9(c) shows a structure through an optical microscope of Co-20Cr-10W-2Nb.

DETAILED DESCRIPTION OF THE PREFERRED EMBODIMENTS

Figure 1:
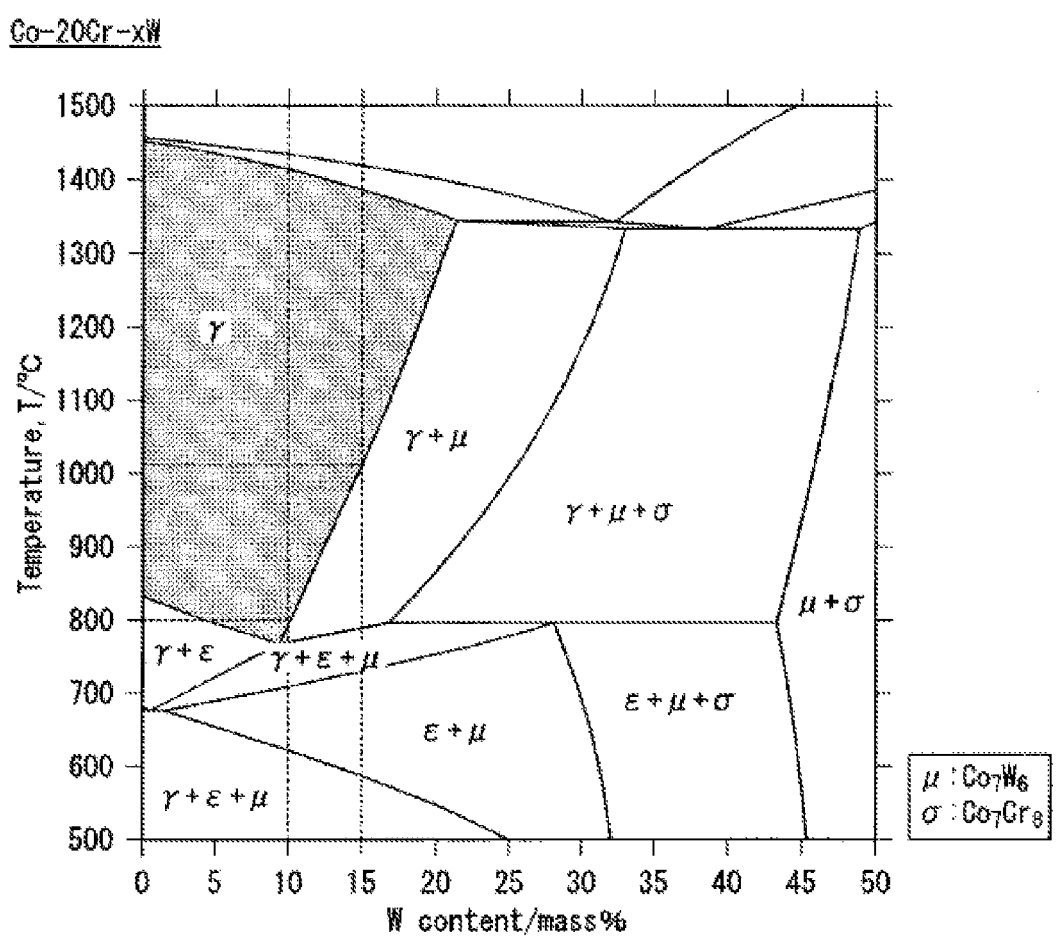
FIG. 1 is a diagram illustrating a calculation state of Co-20Cr-xW alloys.

The inventors of the present invention performed thorough examination in order to develop Co-based alloys for biomedical applications which are Ni free, which have high intensity (high tensile strength), high elastic modulus, high ductility and favorable plastic workability and as a result of the examination, the problems described above can be solved by adding an alloy element which has biocompatibility and which has an effect of causing stacking fault energy to increase in the corresponding alloys to Co—Cr—W system alloys.

Hereinafter, material science consideration according to the present invention will be described.

First, in order to make alloys Ni-free, the inventors of the present invention perform a verification regarding an Ni addition effect of the alloys (ASTM standard F90) which primarily consists of Co-20Cr-15W-10Ni well-known as a material which satisfies a favorable property as an alloy for biomedical applications.

In the Co-based alloys, Ni is a material added to improve plastic workability. The reason is considered as below, that is, through the Ni addition, a γ phase of fcc (face centered cube lattice) structure of the Co-based alloys is stabilized and at the stage of the process, since an ε phase of an hcp structure, which is a strain induction martensite phase is not generated, so that a property of sufficient cold workability is obtained. With respect to the above, the reason that when Ni-free alloys of Co-20Cr-15W-10Ni alloys is made, it is considered that the stability of the cold workability is noticeably lowered since Ni is not added, the stability of the γ phase is lowered and since the ε phase is generated at the early stage of the process, stress concentration is generated on an interface between the γ phase and the ε phase and thereby, destruction which originates from the above is generated.

Accordingly, the inventors considered that alloy composition which makes the γ phase, that is the fcc structure excellent in the plastic workability stable and in which the strain induction martensite ε phase, that is the hcp structure is not generated at the process stage is important and therefore, further verification is carried out focusing on Stacking Fault Energy (SFE) of alloy system which phase-transforms from the γ phase to the ε phase.

A method for calculating the SFE of the alloy system which phase-transforms from the fcc (face centered cube lattice) structure to the hcp (hexagonal closest packing lattice) structure as a thermodynamic aspect is suggested by Olson and Cohen (Metall. Trans. 7A (1976) 1897-1904). According to them, as the stacking fault is assumed to be a thin hcp crystal, the SFE is expressed as following equations as a sum of volume energy term and surface energy term.

[Equation 1]

$$\gamma_{SFE} = 2\rho(\Delta G^{\gamma \to \epsilon} + E^{strain}) + 2\sigma \quad \text{formula (1)}$$

Here, $\Delta G^{\gamma \to \epsilon}$, $E^{strain}$ and $\sigma$ respectively show the Gibbs energy change according to transform from γ to ε, elastic strain energy generated when the ε phase is generated in the γ phase and interface energy of a boundary γ and ε, ρ shows an atomic density per 1 mol of $\{111\}_\gamma$ surface and is calculated as following equation.

[Equation 2]

$$\rho = \frac{4}{\sqrt{3}} \frac{1}{a^2 N} \quad \text{formula (2)}$$

Figure 11A:
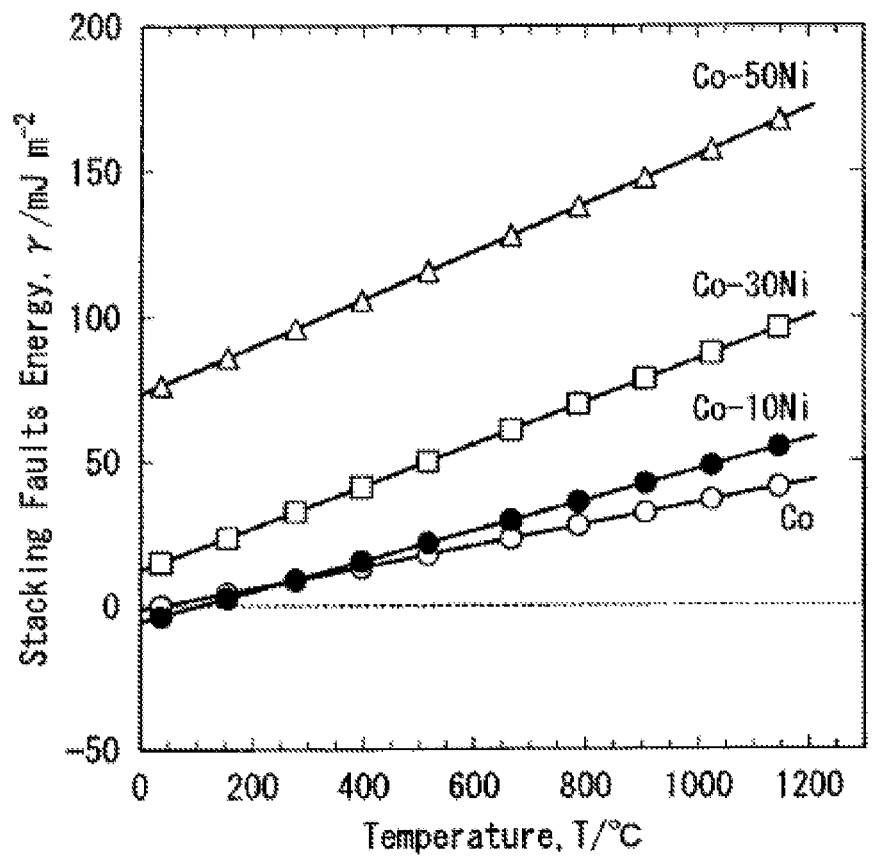
FIGS. 11(a) and 11(b) show graphs which plot stacking fault energy and a temperature calculated using thermodynamic model with respect to FIG. 11(a) Co-xNi alloys and FIG. 11(b) practical Co-based alloys and Fe—Cr—Ni system alloys.

Here, a is a lattice constant of fcc phase and N is Avogadro's number. In a study regarding austenitic steel using formula (1), since a volume change of transformation from γ to ε be small, $E^{strain}$ can be ignored and the elastic strain energy term can be ignored in the same manner as the case of Co alloys. In addition, substantially, there is no temperature dependence for a value of 2σ and the fcc alloys is substantially 15 mJ/m². When only a chemical the Gibbs energy change is considered as the volume energy term by ignoring the change amount of magnetic energy of $\Delta G^{\gamma \to \epsilon}$ of cobalt, temperature dependence and composition dependability of the SFE can be calculated using Thermo-calc (manufactured by Thermo-Calc Software corporation: ver.4.1.3.41, database: FE ver.6) which is generally used thermodynamic calculation software. FIG. 11(a) is a graph showing a temperature change of stacking fault energy (SFE) of alloys in which Ni is added to Co calculated using Thermo-Calc. In addition, a physical property used for SFE calculation is expressed in Table 1. Since the temperature dependence of the interface energy of formula (1) is small and the value in transition metals is not changed, the surface energy term is calculated as $2\sigma^{\gamma/\epsilon} = 15$ mJm$^{-2}$.

TABLE 1

| Symbol | Nomenclature | value |
|---|---|---|
| $2\sigma^{\gamma/\epsilon}$ | Surface energy of the interface γ/ε, mJm$^{-2}$ | 15 |
| a | Lattice constant, nm | 0.354 |
| N | Avogadro's number, mol$^{-1}$ | $6.022 \times 10^{23}$ |

TABLE 1-continued

| Symbol | Nomenclature | value |
|---|---|---|
| G | Shear modulus, GPa | 88 |
| $b_p$ | Magnitude of Burgers vectors of the partial dislocations, nm | 0.145 |
| ν | Poisson's ratio | 0.28 |
| M | Schmid factor | 0.326 |
| γ | Stacking fault energy, mJm$^{-2}$ | |
| | 1050° C. | 29.1 |
| | 1100° C. | 36.2 |
| | 1150° C. | 43.3 |
| | 1200° C. | 50.4 |

As shown in FIG. 11(a), the SFE increases according to increase of the addition amount of Ni to Co. The fact that by adding Ni to Co, the ductility (plastic workability) is improved is well-known, but, the reason that Ni is an element which has an effect of causing the stacking fault energy of the Co-based alloys to increase can be verified.

Figure 11B:
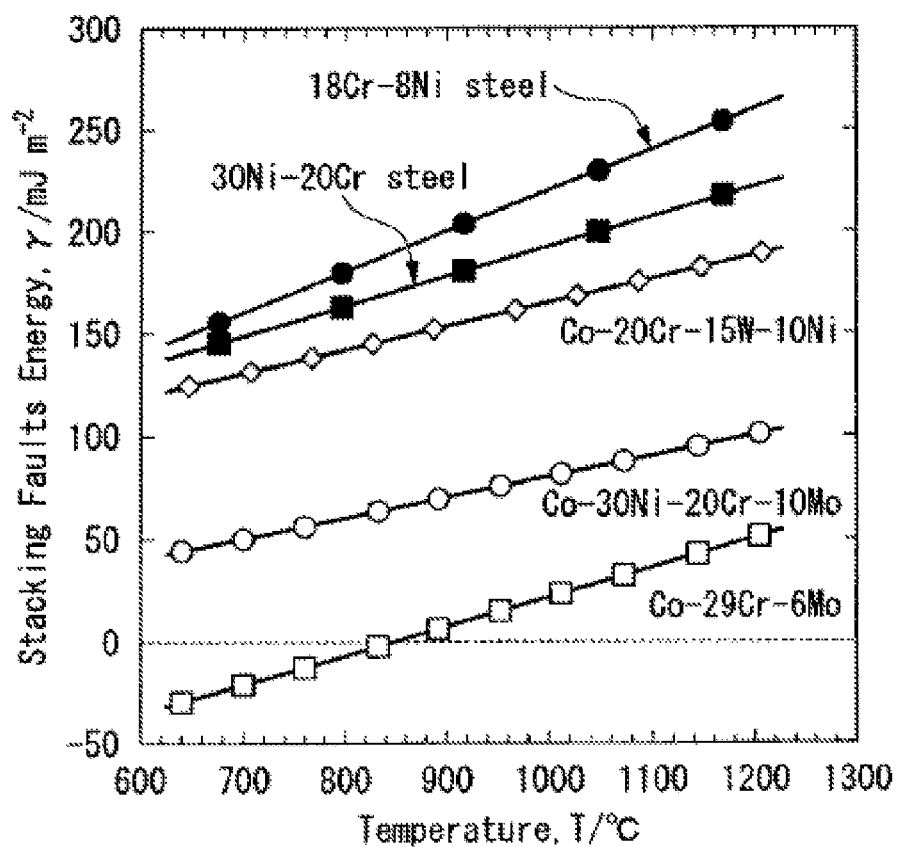

Furthermore, FIG. 11(b) shows a result of calculating a temperature change of the SFE regarding various practical Co-based alloys in the same manner as the calculation method shown in FIG. 11(a). In FIG. 11(b), Co-29Cr-6Mo alloys are alloys used for artificial joints manufactured according to ASTM F75 standard, Co-30Ni-20Cr-10Mo alloys are casting alloys such as a round bar material for biomedical applications manufactured by ASTM F562 standard, Co-20Cr-15W-10Ni is a casting alloy applied as a tube material for biomedical applications manufactured by ASTM F90 standard. In addition, in FIG. 11(b), the thermo-Calc calculation results of SUS 304 austenitic system stainless steel (Fe-30Ni-20Cr) and 800H high nickel steel (Fe-30Ni-20Cr) are also shown.

As shown in FIG. 11(b), the SFE of the Co-based alloys is lower than that of Fe-based alloys. Even among those, the SFE of Co-29Cr-6Mo alloys is substantially 30 mJm$^{-2}$ to 50 mJM$^{-2}$ which is noticeably low, even at 1,050° C. to 1,200° C. Under equal to or less than 850° C., the calculation value of the SFE becomes negative, however, in a temperature region under the temperature, the ε phase is stable and the value of $\Delta G^{\gamma \to \epsilon}$ considerably becomes negative and in such temperature range, it is considered that the high temperature γ phase is in a metastable state. Co-29Cr-6Mo, which is Ni-free-Co—Ni—Mo system alloys, at room temperature, the γ phase of substantially 20% of high temperature phase remains in addition to the ε phase and it is known that Co-29Cr-6Mo is a material having low plastic workability. By adding a very small amount of nitrogen to the alloy compositions, substantially 100% of γ phase remains in the metastable state at room temperature, however, it is known that through the plastic process, a phase change from the γ phase to strain induction martensite ε phase is incurred and a cold rolling processing property is disturbed. Accordingly, it is verified that the plastic workability of the Co-based alloys of low SFE is low.

On the other hand, in each of alloys such as Co-20Cr-30Ni-10Mo alloys, Co-20Cr-15W-10Ni alloys, SUS 304 and 800H high nickel steel, stability of the γ phase or austenite phase of the fcc structure is extremely high compared to that of Co-29Cr-6Mo alloys in the temperature range shown in FIG. 11(b), thereby the values of the SFEs become larger.

Among these Co-based alloys, Co-20Cr-15W-10Ni alloys having large SFE have the same degree of SFE as that of practical alloys classified as low SFE alloys such as austenite stainless steel in addition to the Co alloys. Since the γ phase is in a stable state up to room temperature and mechanically induced martensite ε phase change is hardly incurred, Co-20Cr-15W-10Ni is known as alloys that the plastic workability thereof is excellent at room temperature. Accordingly, it can be verified that the Co-based alloys of large SFE is excellent in the plastic workability.

Furthermore, it is known that Co—Ni—Cr—Mo system alloys represented by Co-20Cr-30Ni-10Mo alloys having an intermediate degree of SFE shows high elastic strength and high intensity, however, it is known that the plastic workability is more degraded than that of Co-20Cr-15W-10Ni and when the Ni addition amount increases, the mechanically induced martensite change is suppressed and thereby, the plastic process such as a cold rolling becomes possible.

According to the result obtained from the above, in the Co-based alloys, since as the SFE becomes larger, the plastic workability is further improved, it can be seen that it is effective to add the element which is effective to improve the SFE to the Co-based alloys to improve the plastic workability of the alloys.

In addition, a tendency is shown that the SFE linearly increases with the temperature in every alloy and the value (substantially 30 mJm$^{-2}$) obtained by extrapolating a calculation result of SUS 304 steel up to room temperature is close to a value reported in the related art. Moreover, temperature dependence of SFE of Co and Co—Ni system alloys is reported (Acta Metall 14 (1966) 853-865) by Ericsson through a method using TEM (transmissive type electron microscope) in the past, the value substantially matches that of Co—Ni system alloys obtained here and SFE of another alloy system structured using the same data base and the temperature dependence thereof can be determined to be reliable.

In the Co-based alloys for biomedical applications according to the present invention, as alloy elements which are added to Co—Cr—W system alloys, alloy elements having biocompatibility and an effect of causing stacking fault energy of the alloys to increase are preferable and among those, it is preferable to add any one of one type or two types or more selected from a group consisting of Nb, Ta and Fe, that is, any one of Nb, Ta and Fe or any one of combination of Nb and Ta, Nb and Fe, Ta and Fe or Nb, Ta and Fe. By adding the alloy elements, it is possible to increase the SFE of the Co-based alloys for biomedical applications and improve the plastic workability and intensity, elastic modulus or the like.

Hereinafter, a method for specifying alloy elements is described.

From formula (1) by estimating the Gibbs energy change $\Delta G^{\gamma \to \epsilon}$ according to γ→ε transition, that is, a difference between free energy of the γ phase and free energy of the ε phase, a roughly calculated value of SFE of alloys can be known to be large or small and it can be seen that the more $\Delta G^{\gamma \to \epsilon}$ is obtained, the more SFE is obtained. Accordingly, by calculating $\Delta G^{\gamma \to \epsilon}$ when adding various elements to Co and examining the value, it is possible to specify an element which is effective in increasing SFE of the Co-based alloys.

Figure 12A:
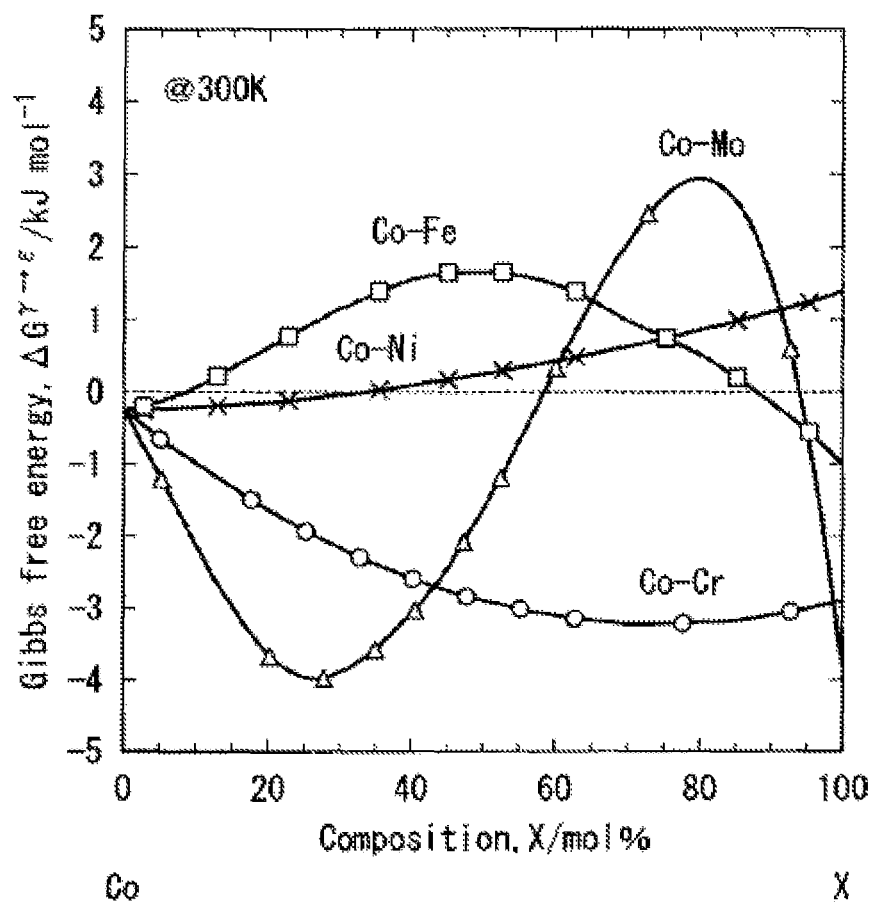
FIGS. 12(a) and 12(b) shows a composition diagram of free energy calculated using thermodynamic model of (a) Co-xX (X=Ni, Cr, Mo and Fe) alloys and (b) Co-xX (X=W, Nb and Ta) alloys.

FIG. 12(a) shows a calculation result of composition dependability of the Gibbs energy change $\Delta G^{\gamma \to \epsilon}$ according to γ→ε transition when adding Ni, Cr, Mo and Fe to Co using Thermo-Calc (manufactured by Thermo-Calc Software Corporation: ver. 4.1.3.41, database: FE ver. 6). As shown in FIG. 12(a), it can be seen that when adding Ni to Co, $\Delta G^{\gamma \to \epsilon}$ increases and by adding Ni, SFE increases. With respect to the above, it can be seen that when adding Cr to Co, $\Delta G^{\gamma \to \epsilon}$ decreases and there is no effect of increasing SFE due to adding Cr. Moreover, when adding Mo to Co, up to 30 mol % of the addition amount, $\Delta G^{\gamma \to \epsilon}$ is lowered, however, when adding more than the above, $\Delta G^{\gamma \to \epsilon}$ increases. However, when considering a practical use property, there are many cases in which substantially 10 mol % of Mo is added to the Co-based alloys for biomedical applications and when adding substantially 10 mol %, $\Delta G^{\gamma \to \epsilon}$ is lowered, thereby it is considered that when adding Mo, SFE is lowered. Furthermore, when adding Fe to Co, up to substantially 50 mol % of the addition amount, $\Delta G^{\gamma \to \epsilon}$ increases and the degree of the increase is larger than that of Ni. From the result, it can be seen that SFE further increases by adding Fe to Co compared to SFE when adding Ni. Accordingly, by adding Fe to Co, it is possible to increase $\Delta G^{\gamma \to \epsilon}$, that is, of increasing SFE and to improve the plastic workability of the alloys.

Figure 12B:
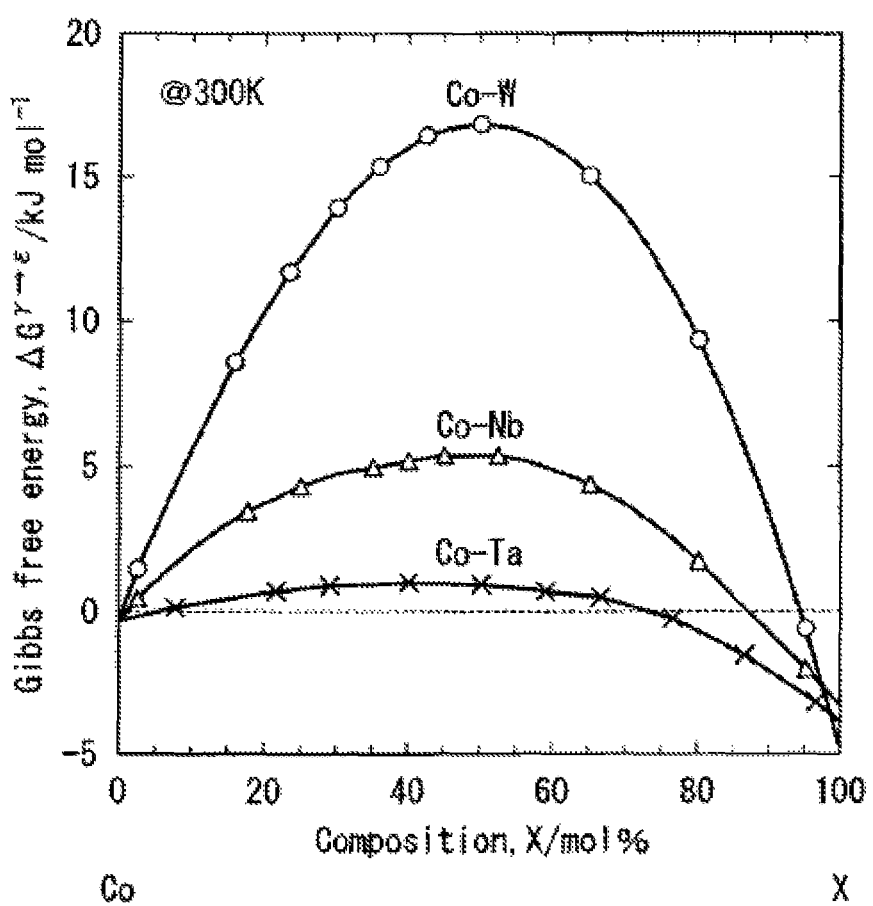

FIG. 12(b) shows a calculation result of composition dependability of the Gibbs energy change $\Delta G^{\gamma \to \epsilon}$ according to the $\gamma \to \epsilon$ transition when W, Nb and Ta are added to Co using the Thermo-Calc. As shown in FIG. 12(b), it can be seen that when W is added to Co, up to 50 mol % of the addition amount, $\Delta G^{\gamma \to \epsilon}$ considerably increases and when W is added to Co, it is possible to increase SFE. Moreover, in the same manner, when Nb is added to Co and Ta is added to Co, up to 50 mol % of the addition amount, it can be seen that $\Delta G^{\gamma \to \epsilon}$ increases and by adding Nb or Ta to Co, it is possible to increase SFE. An increase effect of $\Delta G^{\gamma \to \epsilon}$ when Nb or Ta is added to Co, is smaller than that when W is added to Co. However, as shown in FIG. 11(a), also in the case of Ni which has an effect of causing Co based SFE to increase, as shown in FIG. 12(a), even though the increase degree of $\Delta G^{\gamma \to \epsilon}$ thereof is only substantially 1.5 kJ/mol$^{-1}$ even in a state where most Co—Ni based alloys are substituted for Ni (100 mol % of Ni is added), with respect to the above, by adding a small percentage of Nb to Co, it is possible to obtain the same degree of an increase effect of $\Delta G^{\gamma \to \epsilon}$ as that when 100 mol % of Ni is added and also in a case of Ta, it can be seen that with the addition amount which is considerably smaller compared to the addition amount of Ni, there is an increase effect of $\Delta G^{\gamma \to \epsilon}$. Accordingly, by adding Ni or Ta to Co, it is possible to increase $\Delta G^{\gamma \to \epsilon}$, in other words, to increase SFE and to improve the plastic workability of the alloys. In FIG. 12(b), the result when Nb or Ta is independently added to Co is shown, however, even in a case where Nb and Ta are combined and added, similarly to the above result, it is considered that there is an effect of increasing $\Delta G^{\gamma \to \epsilon}$ and SFE of Co based alloys. In addition, as described above, from the result that through the addition of Fe to Co, there is the effect of increasing $\Delta G^{\gamma \to \epsilon}$ and SFE of the Co-based alloys, even when Nb and/or Ta and Fe are combined and added, similarly to the above result, it is considered that there is an effect of increasing $\Delta G^{\gamma \to \epsilon}$ and SFE of the Co-based alloys. Here, the combinations of Nb and/or Ta and FE mean any one of the combinations of Nb and Fe, Ta and Fe and Nb, Ta and Fe.

From the result described above, in the Co-based alloys for biomedical applications according to the present invention, as alloy elements added to Co—Cr—W system alloys, an alloy element which has biocompatibility and an effect of increasing stacking fault energy of the alloys is preferable and since it is possible to make the alloys be Co-based alloys for biomedical applications which is Ni-free, has high intensity and high elastic strength and is suitable for plastic workability, it is preferable to add one type or two types or more selected from a group consisting of Nb, Ta and Fe. Among those, it is preferable to add any one of Nb or Ta or both Nb and Ta. By adding Nb and/or Ta to the Co—Cr—W system alloys, it is possible to improve the tensile strength of the Co—Cr—W system alloys and the Young's modulus as shown in an embodiment, which will be mentioned later, and it is possible to make Co-based alloys for biomedical applications which is Ni-free, has high intensity and high elastic strength and is suitable for plastic workability. In addition, since Nb and Ta are heavier elements compared to Co, Cr and Ni, the density is high and even when Nb and Ta are processed to have extremely thin thicknesses as alloys for a stent, it is possible to exert high X-ray visibility. Accordingly, the Co-based alloys for biomedical applications are suitable for the stent.

Furthermore, through logical consideration according to the present invention, it is possible to specify an alloy element which has biocompatibility in addition to the above and exerts an effect which can increase SFE and improve ductility (plastic workability) of the Co—Cr—W system alloys in the same manner as the above.

The Co-based alloys for biomedical applications according to the present invention preferably contains the following, Cr: 5% by mass to 30% by mass and W: 5% by mass to 20% by mass.

FIG. 1 is a diagram illustrating a calculation state using Thermo-Calc (manufactured by Thermo-Calc Software Corporation: ver. 4.1.3.41, database: FE ver. 6) of Co-20Cr-xW alloys. As shown in FIG. 1, in a case where the contained amount of W is less than 20% by mass, the γ phase of the fcc structure is stabilized. As described above, when considering that W has an effect of increasing SFE of the Co-based alloys and to improve plastic workability, the contained amount of W is preferably 5% by mass to 20% by mass and is more preferably 10% by mass to 15% by mass. When the addition amount of W exceeds 20% by mass, there is a possibility that a μ phase ($Co_7W_6$), a σ phase ($Co_7Cr_8$) or the like may be incurred and mechanical properties may be degraded. Moreover, by adding W, it is possible to increase the density of the alloys and increase solute strengthening and furthermore, it is possible to increase X-ray visibility.

Figure 2A:
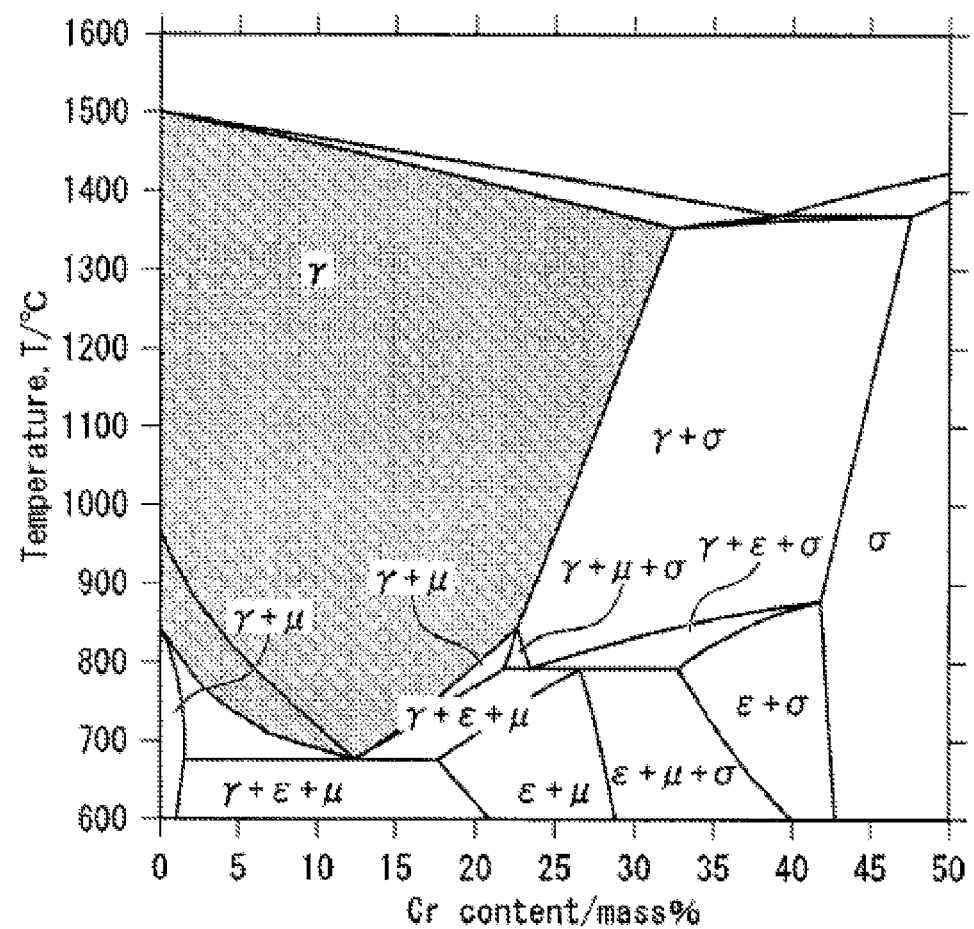
FIG. 2(a) is a diagram illustrating a calculation state of Co-xCr-10W alloys and FIG. 2(b) is a diagram illustrating a calculation state of Co-xCr-15W alloys.
Figure 2B:
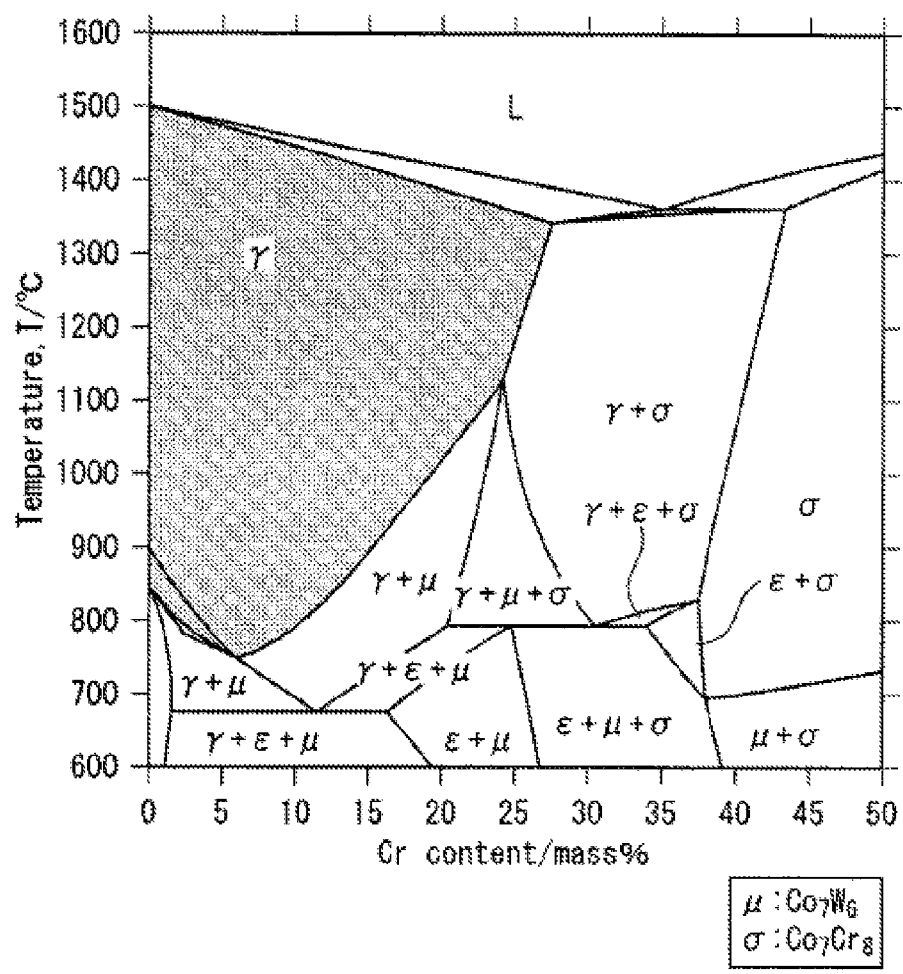

FIG. 2(a) is a diagram illustrating a Thermo-Calc calculation state of Co-xCr-10W alloys and FIG. 2(b) is a diagram illustrating a Thermo-Calc calculation state of Co-xCr-15W alloys. As shown in FIG. 2(a) and FIG. 2(b), since the γ phase of the fcc structure is stabilized and phase transition at the process stage is suppressed, the contained amount of Cr is preferably 5% by mass to 30% by mass and is more preferably 16% by mass to 25% by mass from the viewpoint of increasing corrosion resistance of the alloys. When the addition amount of Cr exceeds 30% by mass, there is a possibility that a μ phase ($Co_7W_6$), a σ phase ($Co_7Cr_8$) or the like may be incurred and mechanical properties may be degraded.

Furthermore, in the Co-based alloys for biomedical applications according to the present invention, it is preferable that the addition amount of Nb and Ta or both Nb and Ta, which are the alloy elements, is less than 3% by mass.

Figure 3A:
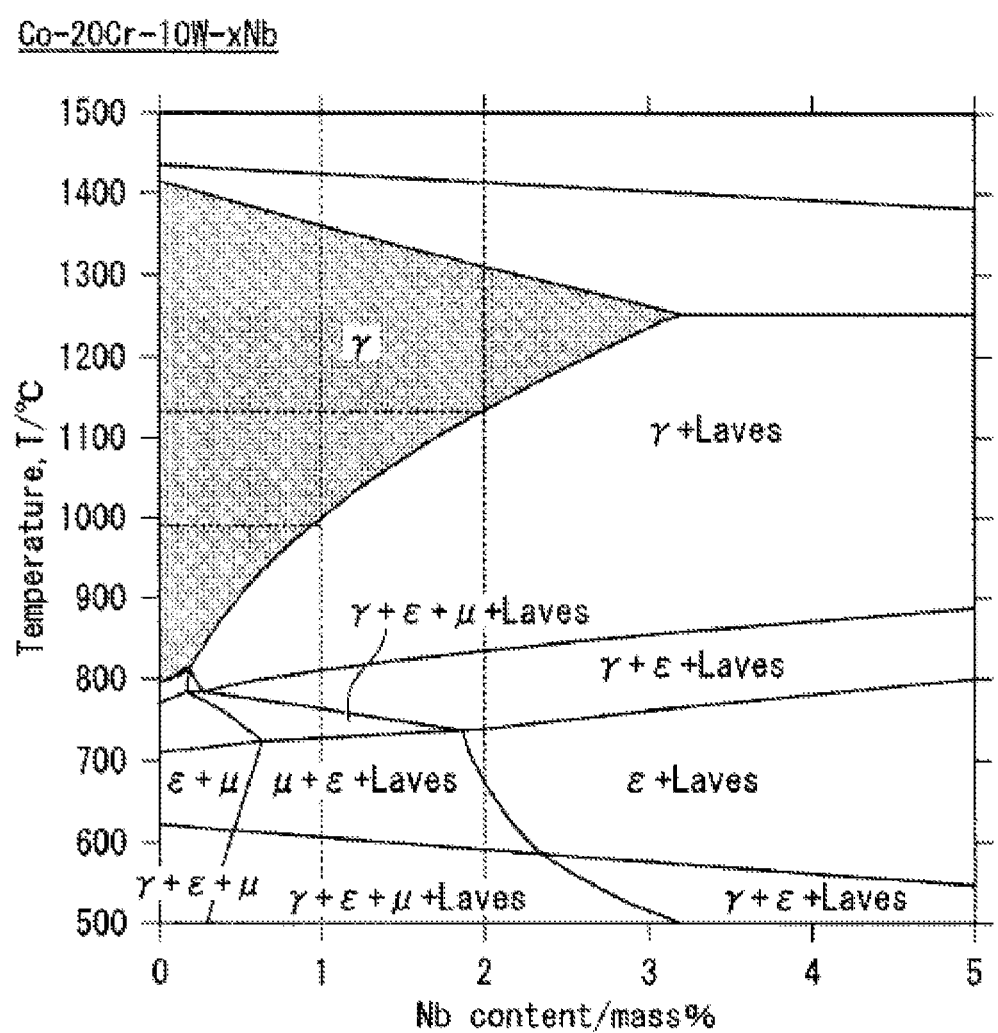
FIG. 3(a) is a diagram illustrating a calculation state of Co-20Cr-10W-xNb alloys and FIG. 3(b) is a diagram illustrating a calculation state of Co-20Cr-15W-xNb alloys.
Figure 3B:
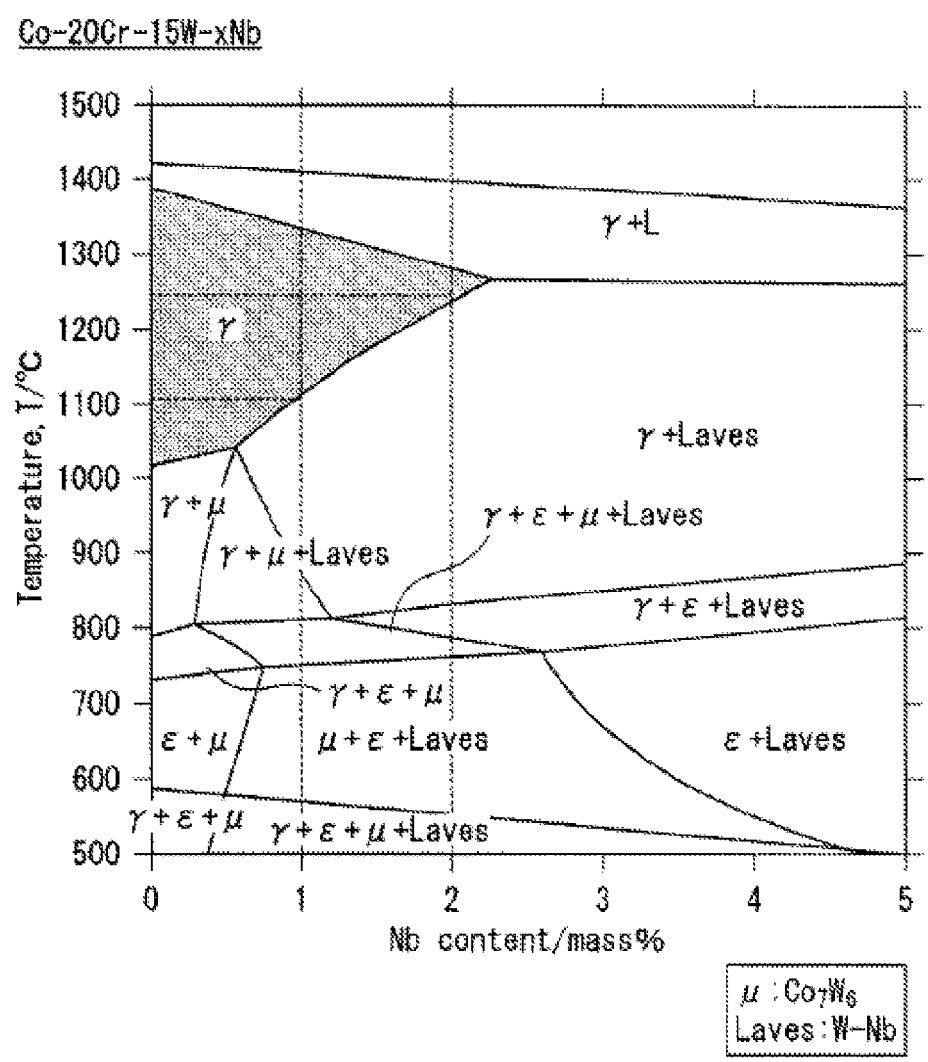

FIG. 3(a) is a diagram illustrating a Thermo-Calc calculation state of Co-20Cr-10W-xNb alloys and FIG. 3(b) is a diagram illustrating a Thermo-Calc calculation state of Co-20Cr-15W-xNb alloys. As shown in FIG. 3(a) and FIG. 3(b), since the γ phase of the fcc structure is stabilized and phase transition at the process stage is suppressed, the addition amount of Nb is preferably less than 3% by mass and is more preferably 1% by mass to 2% by mass. When the addition amount of Nb exceeds 3% by mass, there is a possibility that a μ phase ($Co_7W_6$), a Laves (W—Nb) or the like may be incurred and mechanical properties may be degraded.

Figure 4A:
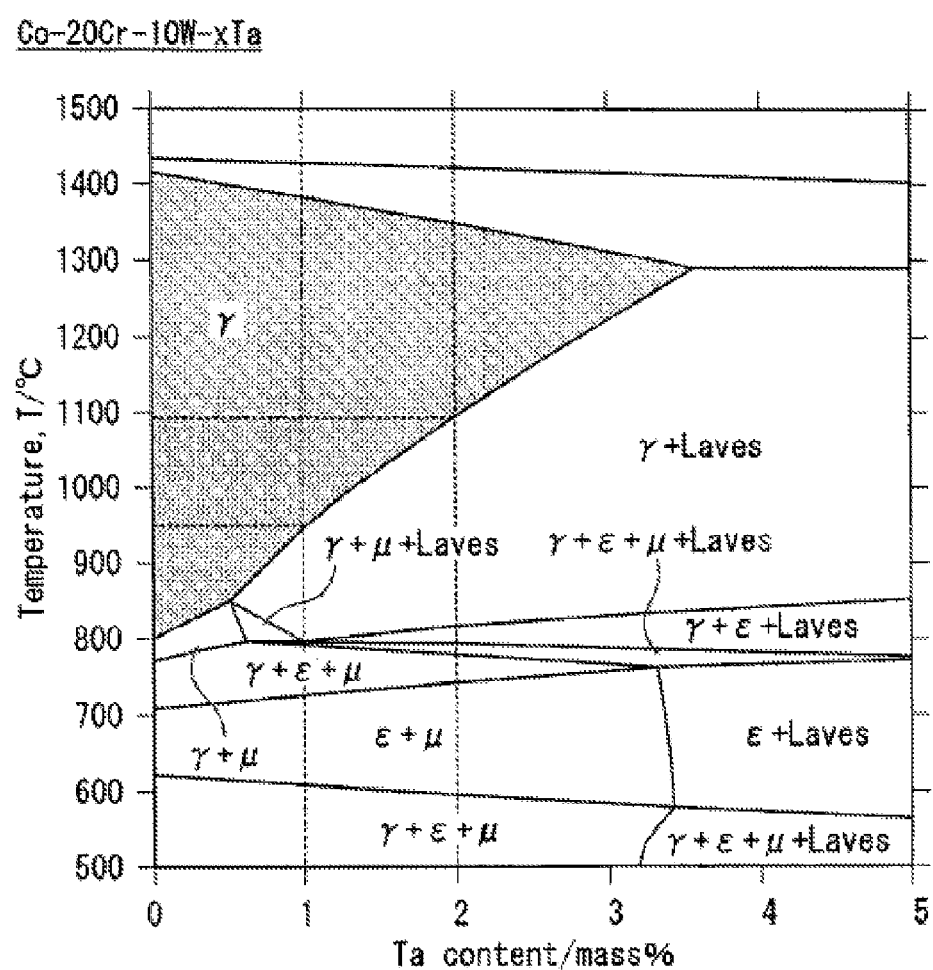
FIG. 4(a) is a diagram illustrating a calculation state of Co-20Cr-10W-xTa and FIG. 4(b) is a diagram illustrating a calculation state of Co-20Cr-15W-xTa.
Figure 4B:
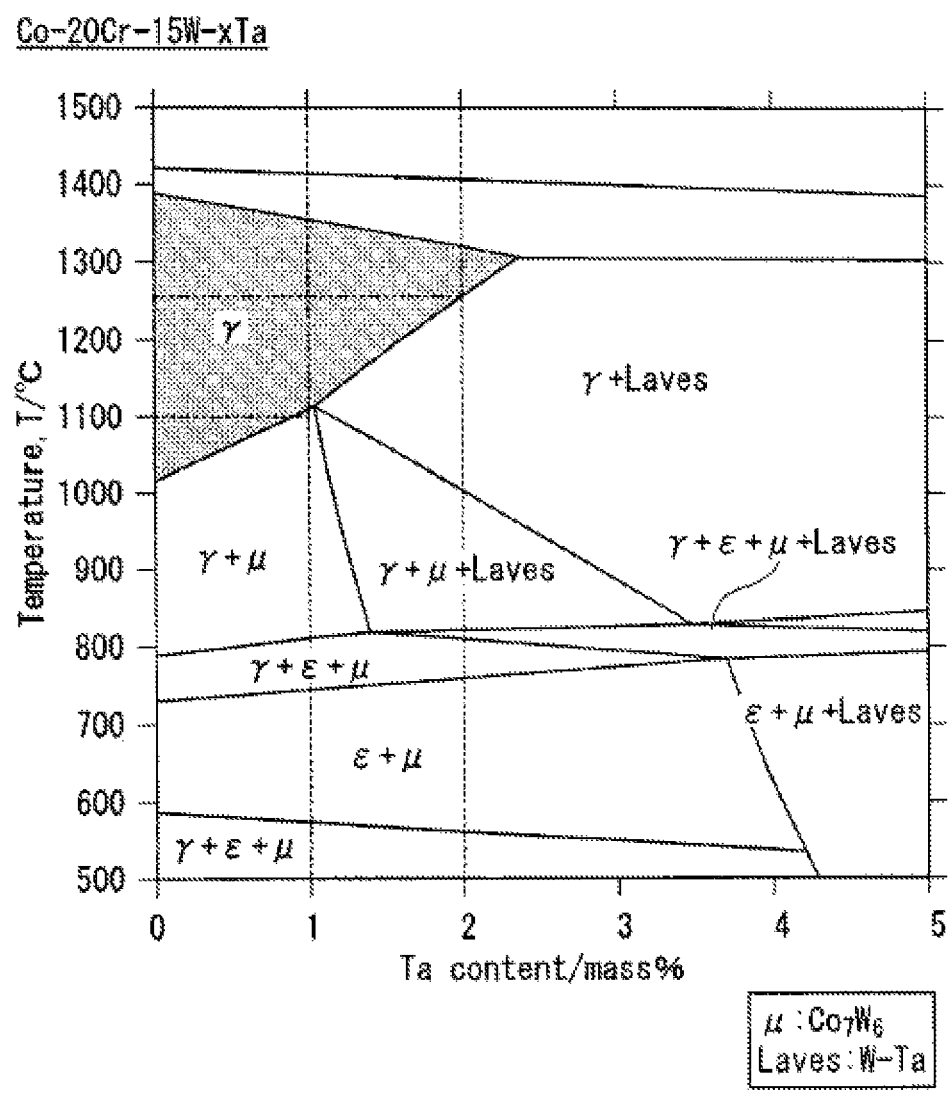

FIG. 4(a) is a diagram illustrating a Thermo-Calc calculation state of Co-20Cr-10W-xTa alloys and FIG. 4(b) is a diagram illustrating a Thermo-Calc calculation state of Co-20Cr-15W-xTa alloys. As shown in FIG. 4(a) and FIG. 4(b), since the γ phase of the fcc structure is stabilized and phase transition at the process stage is suppressed, the addition amount of Ta is preferably less than 3% by mass and is more preferably 1% by mass to 2% by mass. Since there is a possibility that a μ phase ($Co_7W_6$), a Laves (W—Ta) or the like may be incurred and mechanical properties may be degraded, a case where the addition amount of Ta exceeds 3% by mass is not preferable.

In addition, even when Nb and Ta are combined and added to Co—Cr—W alloys, by setting the addition amount of the alloy elements to be less than 3% by mass, the γ phase of the fcc structure is stabilized and the plastic workability is improved.

In addition, in the Co-based alloys for biomedical applications according to the present invention, it is preferable to add Fe to Co—Cr—W system alloys. Fe is an element having biocompatibility and moreover, as shown in FIG. 12(a), is an element which, by being added to Co, has an effect of increasing $\Delta G^{\gamma \to \epsilon}$, that is, of increasing SFE. Accordingly, by adding Fe to Co—Cr—W system alloys, it is possible to improve the plastic workability of the alloys. Since the γ phase of the fcc structure is stabilized and phase transition at the process stage is suppressed, the addition amount of Fe is preferably 5% by mass to 20% by mass.

Here, when Nb and/or Ta in addition to Fe are added to Co—Cr—W based alloys, from a viewpoint of solute strengthening, the total addition amount of the alloy elements is preferably 6% by mass to 23% by mass.

In the Co-based alloys for biomedical applications according to the present invention, by adding alloy elements which has biocompatibility and an effect of increasing stacking fault energy (SFE) of the alloys to Co—Cr—W system alloys, it is possible to stabilize the γ phase of the alloys, prevent the occurrence of strain induction martensite ε phase at the process stage and improve the plastic workability. Moreover, since Ni is not contained in the Co-based alloys for biomedical applications according to the present invention, there is no concern that allergies caused by Ni to a living body may be incurred.

Furthermore, by making the Co-based alloys for biomedical applications according to the present invention by adding one type or two types or more selected from a group consisting of Nb, Ta or Fe to Co—Cr—W system alloys, it is possible to improve not only the plastic workability of the Co-based alloys but also improve elastic modulus and tensile strength. Moreover, since the elements such as Nb and/or Ta, having a high density, are added, X-ray visibility of the alloys can be increased and the alloys are suitable for a stent.

Next, a stent according to the present invention will be described.

Figure 13:
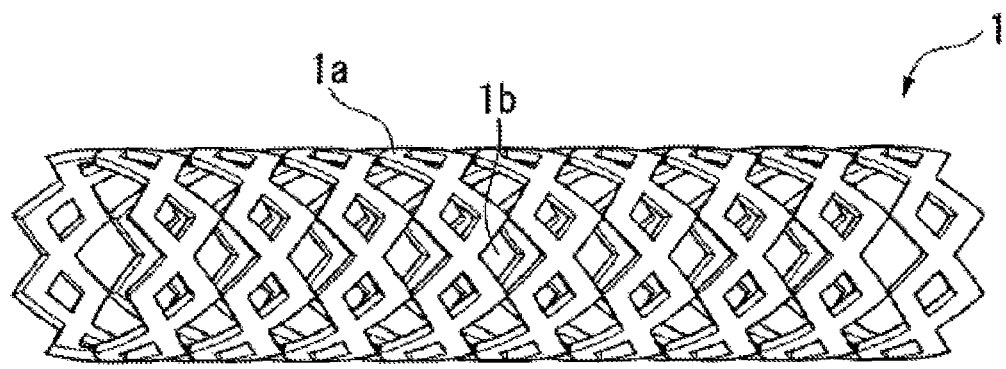
FIG. 13 is a schematic perspective diagram illustrating an example of a stent according to the present invention.

The stent according to the present invention is used to be inserted in a coarctation site of a blood vessel, biliary duct or the like within a living body and to maintain the diameter of a lumen by expanding the lumen and is characterized that the stent is configured to use the Co-based alloys for biomedical applications according to the present invention described above. FIG. 13 is a schematic perspective diagram illustrating an example of the stent according to the present invention. The stent 1 shown in FIG. 13 has a cylindrical structure which is configured such that the diameter can be deformed to be expanded and reduced by a frame 1a. The stent 1 has a mesh-shaped structure having a plurality of notch portions 1b, which is substantially rhombic shaped, on a lateral surface on which the cylindrical structure is formed and by applying stress, the diameter can be deformed to be expanded and reduced. The stent 1 shown in FIG. 13 is a balloon dilatation type stent and in a state where a balloon catheter is fixed inside the cylindrical stent 1, it is possible to come into contact with and fixed to the inner surface of a target site by performing plastic deformation by expansion of the balloon after inserting the stent 1 in the target site.

According to the manufacturing method of the stent 1 of such structure, for example, the stent 1 can be manufactured through a process in which after a pipe of which a length, a diameter, a wall thickness or the like is a predetermined dimension is formed from the Co-based alloys for biomedical applications according to the present invention, the lateral surface of the pipe is partially removed through a cutting process or the like and the plurality of notch portions 1b is formed.

In FIG. 13, a mesh-shaped figure is exemplified as a shape of the frame 1a of the stent 1 which enables the diameter to be deformed to be expanded and reduced, however, the present invention is not limited to the example. For example, a shape of the well-known stent in the related art such as coil-shape or multiple spiral may be applied and a balloon dilatation type stent or self-expansion type stent may be applied.

Since the stent according to the present invention is configured using the Co-based alloys for biomedical applications according to the present invention described above, allergies caused by Ni are not incurred, and the stent has excellent elastic strength and tensile strength. In addition, since the stent is configured of the Co-based alloys for biomedical applications according to the present invention in which Nb and/or Ta is added, the stent can have superior X-ray visibility.

Embodiment

Hereinafter, the present invention will be further described in detail with reference to embodiments, however, the present invention is not limited to the following embodiments.

Alloys of embodiments 1 to 4 and comparison examples 1 to 4 in which each of components of alloy elements are composed as shown in Table 2 are manufactured using the points below.

In a high frequency vacuum induction melting furnace, each of components of the alloy elements was combined as shown in Table 2 and was melted to form alloy molten metal. Under Ar atmosphere of 800 Pa, the alloy molten metal was casted into a metallic mold and furnace cooling was carried out. The size of the cylindrical ingot is such that the upper diameter is 80 mm and the lower diameter is 70 mm, the height is 120 mm and the weight is 6 Kg. Next, in order to remove solidification segregation, a homogenization process was carried out to ingots at 1220° C. in an Ar atmosphere and for 10 hours using a high temperature high vacuum furnace manufactured by Tokyo Vacuum Corporation and subsequently, each of alloys was manufactured by performing the furnace cooling to room temperature. Here, the programming rate during the homogenization process is 10° C./min and the cooling rate is 10° C./min.

TABLE 2

| | | component composition (% by mass) | | | | | |
|---|---|---|---|---|---|---|---|
| | Samples | Co | Cr | W | Nb | Ni | Mo |
| Embodiment 1 | Co—20Cr—10W—1Nb | remaining | 20 | 10 | 1 | | |
| Embodiment 2 | Co—20Cr—10W—2Nb | remaining | 20 | 10 | 2 | | |

TABLE 2-continued

| | Samples | component composition (% by mass) | | | | | |
|---|---|---|---|---|---|---|---|
| | | Co | Cr | W | Nb | Ni | Mo |
| Embodiment 3 | Co—20Cr—15W—1Nb | remaining | 20 | 15 | 1 | | |
| Embodiment 4 | Co—20Cr—15W—2Nb | remaining | 20 | 15 | 2 | | |
| Comparison Example 1 | Co—20Cr—10W | remaining | 20 | 10 | | | |
| Comparison Example 2 | Co—20Cr—15W | remaining | 20 | 15 | | | |
| Comparison Example 3 | Co—20Cr—15W—10Ni | remaining | 20 | 15 | | 10 | |
| Comparison Example 4 | Co—28Cr—6Mo | remaining | 20 | | | | 6 |

1. Measuring Young's Modulus

With respect to each of obtained samples, the Young's modulus was measured by a free resonance method using JE-RT manufactured by Nihon Techno-Plus Corp. The results are shown in FIG. 5.

Figure 5:
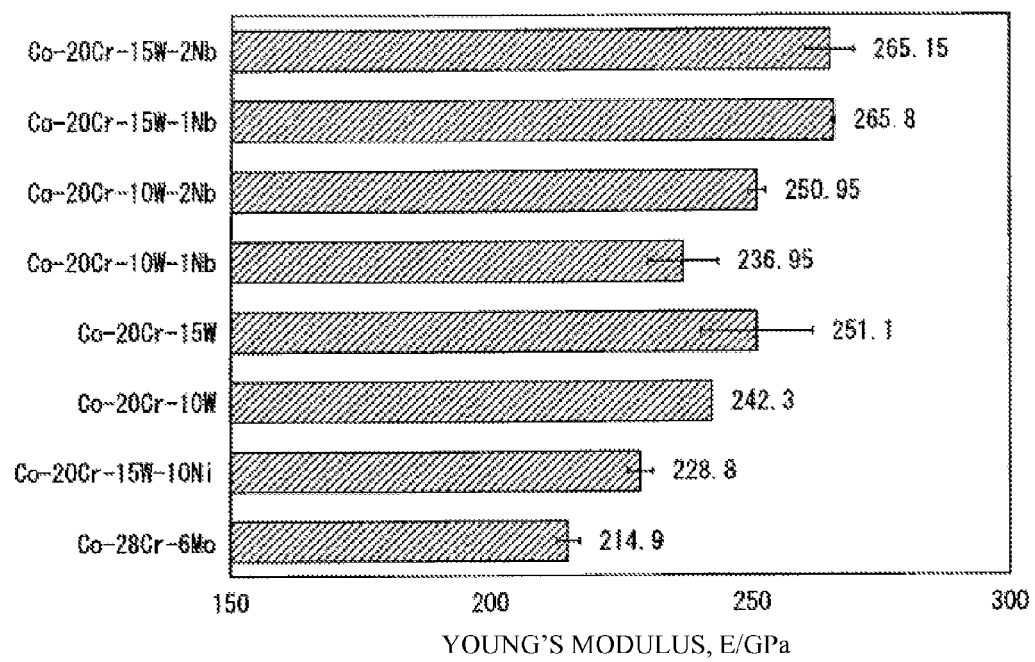
FIG. 5 is a graph illustrating the Young's modulus of alloys of the Embodiments and Comparison examples.

From the results shown in FIG. 5, Co-28Cr-6Mo alloys of the comparison example 4 are alloys used for artificial joints and the Young's modulus thereof is 214.9 GPa. With respect to the above, in Co-20Cr-(10-15) W alloys in the comparison examples 1 and 2 the young's modulus more increases compared to that in the comparison example 4 and it can be seen that by adding W, a high elastic modulus is obtained. Moreover, in alloys to which Ni is added in the comparison example 3, the Young's modulus is lowered compared to that of the alloys in the comparison examples 1 and 2. In alloys of the embodiments 1 to 4, it is verified that by adding Nb to Co—Cr—W alloys, the Young's modulus increases and adding Nb contributes to improving the high elastic modulus.

2. Tensile Test

Figure 6:
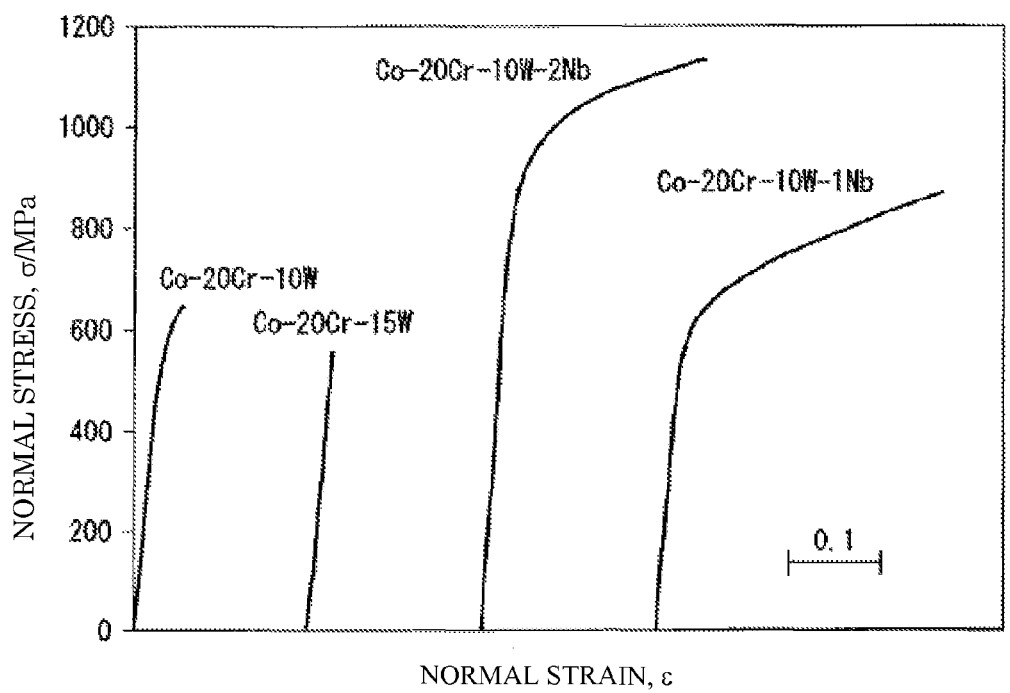
FIG. 6 is a graph illustrating a tensile test result of alloys of the Embodiments and Comparison examples.

A tensile test was carried out to the alloys of embodiments 1 and 2 and the comparison examples 1 and 2 after constant temperature casting at room temperature. The results are shown in FIG. 6 and Table 3. In addition, test conditions are as below:

Test Piece Thickness: 1.0 mm, Width: 2.0 mm
Initial strain rate: $1.4 \times 10^{-4}$ $S^{-1}$
Distance between gauge marks: 11.5 mm
Testing apparatus: manufactured by Instron Corporation, 8562 type tension testing apparatus

TABLE 3

| | | Maximum tensile strength [Mpa] | 0.2% Yield strength [Mpa] | Expansion [%] |
|---|---|---|---|---|
| Embodiment 1 | Co—20Cr—10W—1Nb | 870 | 720 | 16 |
| Embodiment 2 | Co—20Cr—10W—2Nb | 1,138 | 843 | 13 |
| Comparison Example 1 | Co—20Cr—10W | 650 | 541 | 2.8 |
| Comparison Example 2 | Co—20C—15W | 563 | — | 1.5 |

From the results in FIG. 6 and Table 3, in Co-20Cr-(10-15) W alloys in the comparison examples 1 and 2, the ductility thereof is lowered after the constant temperature casting, however, in the alloys in the embodiments 1 and 2 in which 1% or 2% of Nb is added, the ductility increases.

From the result described above, it is verified that the alloys according to the present invention is excellent in ductility and is favorable for plastic workability.

3. Structure Observation and Phase Identification

After a homogenization thermal process of alloys in the embodiments 1 and 2 and the comparison example 1 was carried out at 1,250° C. and for 12 hours, structures of each alloy were observed with an optical microscope. Optical microscope pictures of each alloy are shown in FIG. 7.

Figure 7A:
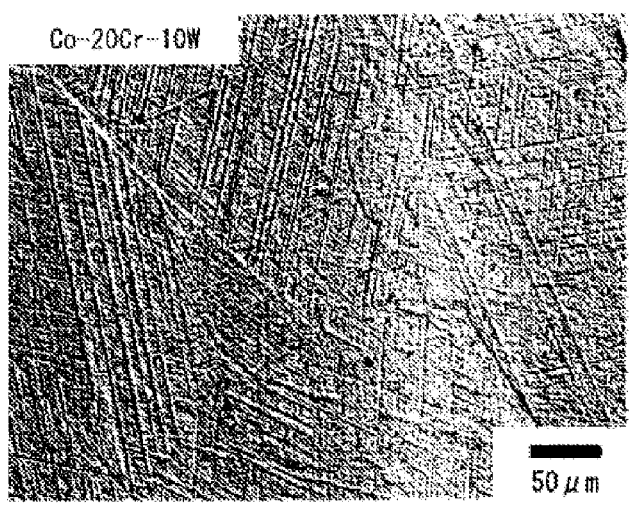
FIGS. 7(a) to 7(c) show photographs illustrating structures through an optical microscope of the alloys of the Embodiments and Comparison examples after an uniform thermal process.
Figure 7B:
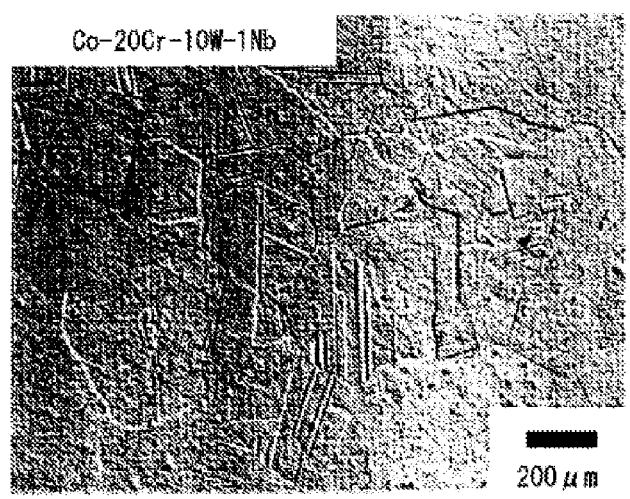
Figure 7C:
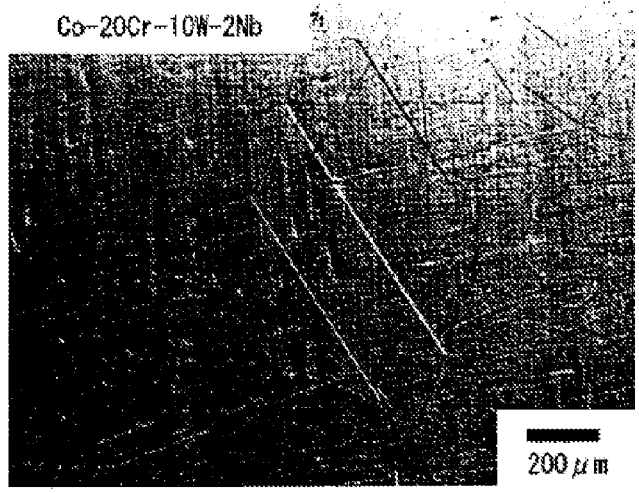

As shown in FIG. 7, every alloy in the embodiments 1 and 2 and the comparison example 1 has a crystal particle diameter of substantially 300 μm to 400 μm of an isometric system.

Figures 8A, 8B, 8C:
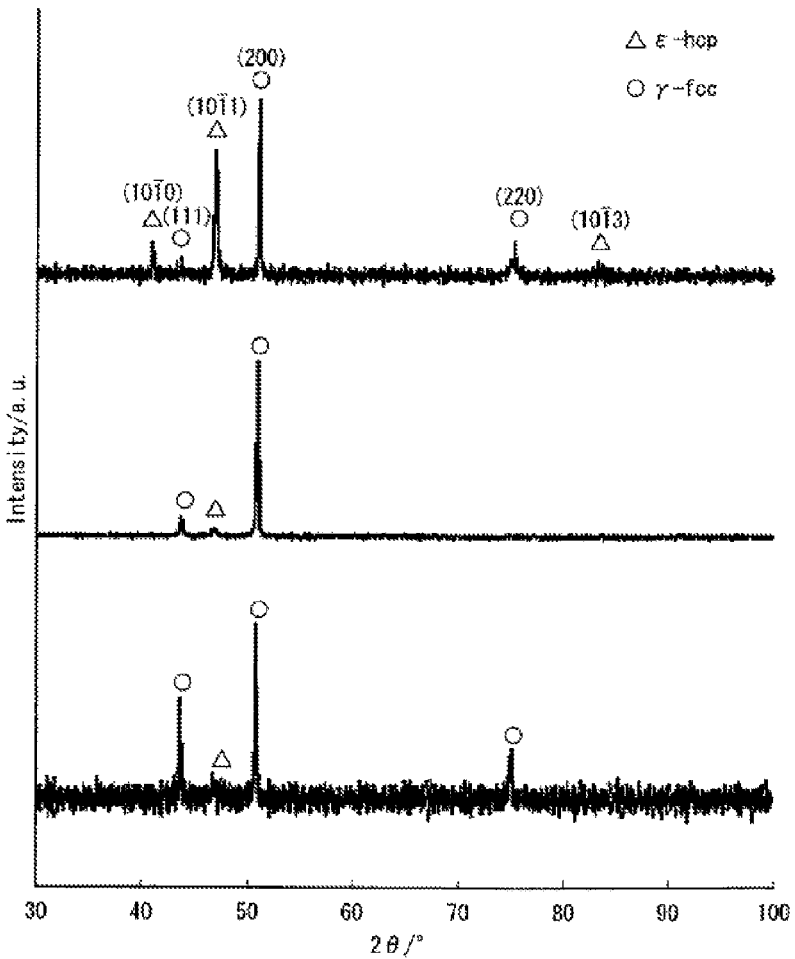
FIGS. 8(a) to 8(c) show X-ray diffraction figures of each alloy shown in FIG. 7(a) to FIG. 7(c).

In addition, with respect to the alloys in which the homogenization process was carried out under the same condition in the embodiments 1 and 2 and the comparison example 1, X-ray diffraction measurement was carried out with an X-ray diffractometer (XRD). The result is shown in FIGS. 8(a) to 8(c). In addition, in FIGS. 8(a) to 8(c), (a) shows X-ray diffraction figure of Co-20Cr-10W alloys in the comparison example 1, (b) shows X-ray diffraction figure of Co-20Cr-10W-1Nb alloys in the embodiment 1 and (c) shows X-ray diffraction figure of Co-20Cr-10W-2Nb alloys in the embodiment 2.

From the result in FIG. 8, the Co-20Cr-10W alloys in the comparison example 1 become two-phase structures in which a peak of the ε phase of the hcp structure and a peak of the γ phase of the fcc phase are mixed. With respect to the above, in the Co-20Cr-10W-1Nb alloys in the embodiment 1 and the Co-20Cr-10W-2Nb alloys in the embodiment 2, a little of the peak of the ε phase is verified, however, the diffraction peak primarily consists of the peak of the γ phase. From the result, it can be seen that through the addition of Nb to Co—Cr—W system alloys, the γ phase is stabilized.

After the homogenization thermal process was carried out at 1,250° C. and for 12 hours with respect to the alloys in the embodiments 1 and 2 and the comparison example 1, constant casting was carried out at 1,100° C., a structure control was carried out, and then, structures of the obtained each alloy are observed with the optical microscope. The optical microscope structure photographs of each alloy are shown in FIG. 9.

Figure 9A:
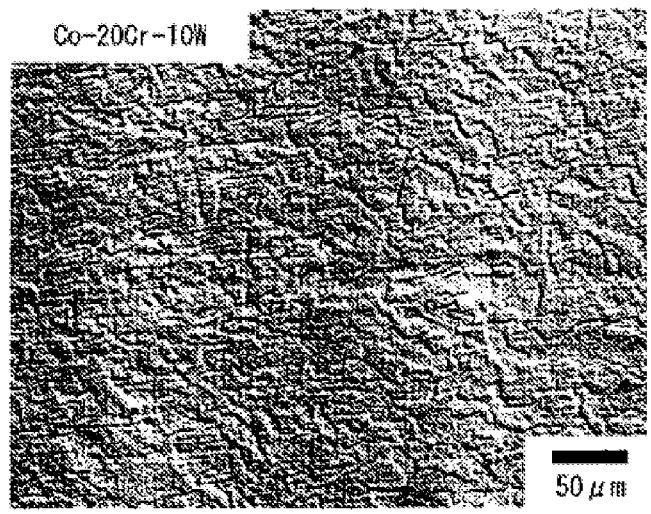
FIGS. 9(a) to 9(c) show photographs illustrating structures through an optical microscope of the alloys of the Embodiments and Comparison examples in which constant temperature casting is carried out after the uniform thermal process.
Figure 9B:
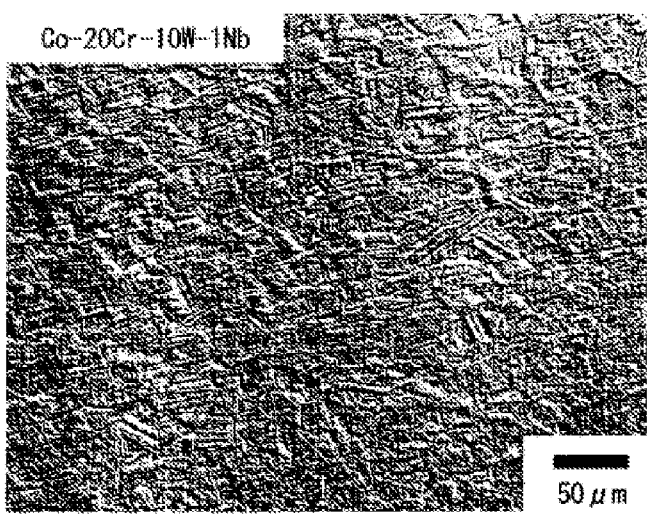
Figure 9C:
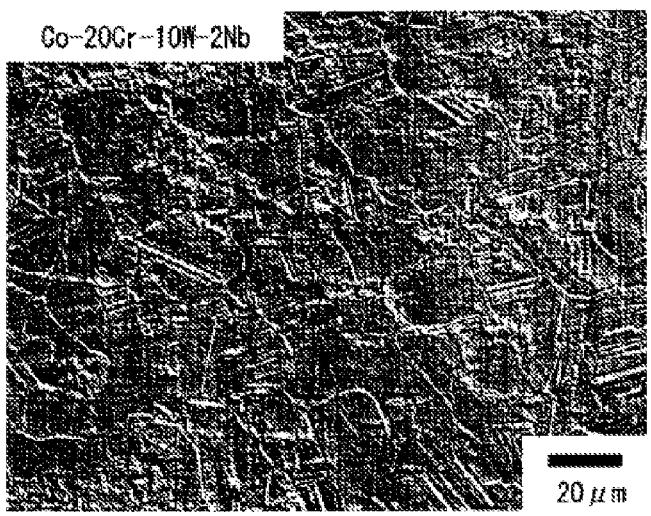

As shown in FIG. 9, every alloy in the embodiments 1 and 2 and the comparison example 1 becomes fine crystal particle structure of substantially 50 μm of the isometric system.

Figures 10A, 10B, 10C:
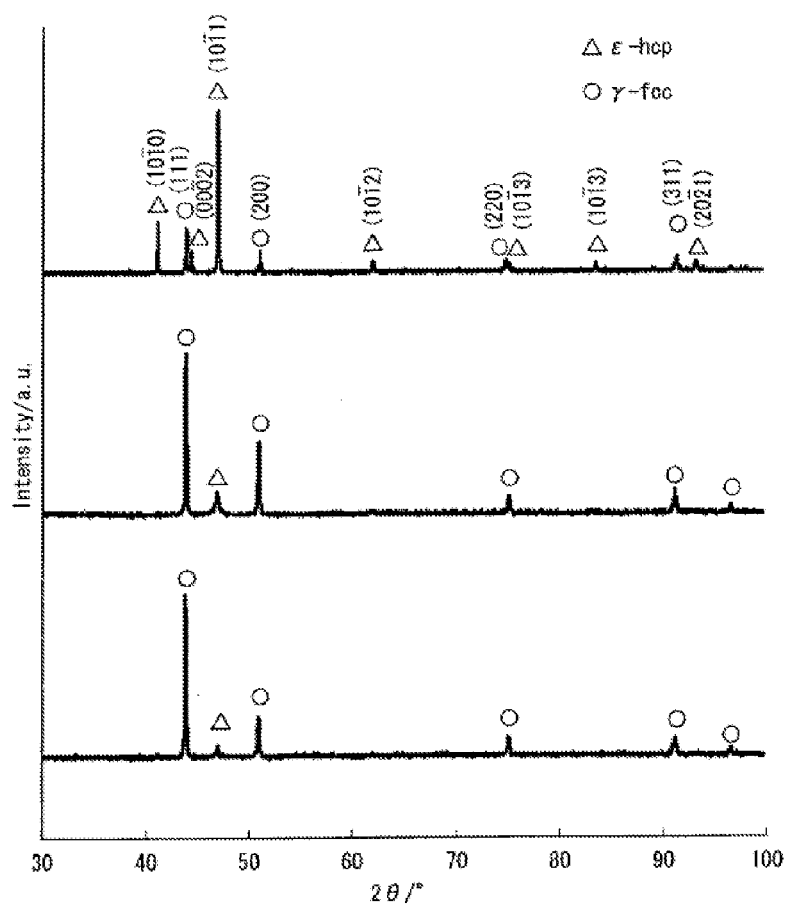
FIGS. 10(a) to 10(c) show X-ray diffraction figures of each alloy shown in FIG. 9(a) to FIG. 9(c).

In addition, X-ray diffraction measurement was carried out with an X-ray diffractometer (XRD) with respect to the alloys in the embodiments 1 and 2 and the comparison example 1 in which after the homogenization thermal process was carried out under the same condition, the constant casting was carried out. The result is shown in FIGS. 10(a) to 10(c). Moreover, in FIGS. 10(a) to 10(c), (a) shows a X-ray diffraction figure of Co-20Cr-10W alloys in the comparison example 1, (b) shows X-ray diffraction figure of Co-20Cr-10W-1Nb alloys in the embodiment 1 and (c) shows X-ray diffraction figure of Co-20Cr-10W-2Nb alloys in the embodiment 2.

From the result in FIGS. 10(a) to 10(c), the Co-20Cr-10W alloys in the comparison example 1 become two-phase structures in which the peak of the $\epsilon$ phase of the hcp structure and the peak of the $\gamma$ phase of the fcc structure are mixed. It can be seen that a ratio of the $\epsilon$ phase is particularly higher compared to that of the $\gamma$ phase. With respect to the above, in the Co-20Cr-10W-1Nb alloys in the embodiment 1 and the Co-20Cr-10W-2Nb alloys in the embodiment 2, a little of the peak of the $\epsilon$ phase is verified, however, the diffraction peak primarily consists of the $\gamma$ phase. The result noticeably suggests that through the addition of Nb to Co—Cr—W system alloys, the $\gamma$ phase is stabilized as in the homogenization thermal processed materials.

The Co-based alloys for biomedical applications according to the present invention can be suitably used for medical equipment which is embedded-in a living body and for medical equipment used by directly contacting on a surface of a living body. For example, the Co-based alloys for biomedical applications of the present invention can be utilized for various uses such as dentist's wires, catheter guide wires, stents, lead wires of pacemaker, valves for mechanical heart, diaphragm, volts for fixing of bone fracture sites, nuts, artificial bones, artificial joints, or the like.

What is claimed is:

1. A stent formed using a Co-based alloy for biomedical applications wherein the Co-based alloy consists of from 68% to 69% by mass Co, 20% by mass Cr, 10% by mass W, and from 1% to 2% by mass Nb or from 1% to 2% by mass Ta.

* * * * *